US00PP33662P2

(12) United States Plant Patent
Niesing

(10) Patent No.: US PP33,662 P2
(45) Date of Patent: Nov. 23, 2021

(54) ***PHOTINIA* PLANT NAMED 'LITTLE FENNA'**

(50) Latin Name: ***Photinia* x *fraseri***
Varietal Denomination: Little Fenna

(71) Applicant: Fa. J.C. Niesing vof, Boskoop (NL)

(72) Inventor: Sebastian Niesing, Boskoop (NL)

(73) Assignee: FA. J.C. NIESING VOF, Boskoop (NL)

( * ) Notice: Subject to any disclaimer, the term of this patent is extended or adjusted under 35 U.S.C. 154(b) by 0 days.

(21) Appl. No.: 17/194,213

(22) Filed: Mar. 6, 2021

(51) Int. Cl.
*A01H 5/02* (2018.01)
*A01H 6/74* (2018.01)

(52) U.S. Cl.
USPC ..... Plt./226
CPC ..... *A01H 6/74* (2018.05)

(58) Field of Classification Search
USPC ..... Plt./226
CPC ..... A01H 6/74; A01H 5/02
See application file for complete search history.

*Primary Examiner* — Keith O. Robinson
(74) *Attorney, Agent, or Firm* — Penny J. Aguirre

(57) ABSTRACT

A new cultivar of *Photinia* plant named 'Little Fenna' that is characterized by its short plant height, its compact and very well-branched plant habit with dense foliage, its sturdy branches that are not prone to flopping and its new growth that is pink in color.

2 Drawing Sheets

Botanical classification: *Photinia* x *fraseri*.
Variety denomination: 'Little Fenna'.

CROSS REFERENCE TO A RELATED APPLICATION

This application is related to a European plant breeders' rights application filed on Jun. 4, 2019, application No. 2019/1363. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Photinia* x *fraseri* and will be referred to hereafter by its cultivar name, 'Little Fenna'. 'Little Fenna' is a new cultivar of an evergreen shrub for use as a landscape plant.

The Inventor discovered the new cultivar in April of 2016 as a naturally occurring branch mutation of *Photinia* 'Little Red Robin' (not patented) that was growing in a container at a nursery in Boskoop, The Netherlands.

Asexual propagation of the new cultivar was first accomplished using semi-hardwood stem cuttings by the Inventor in Boskoop, The Netherlands in 2016. Asexual propagation by semi-hardwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Little Fenna' as unique cultivar of *Photinia*.

1. 'Little Fenna' exhibits a short plant height.
2. 'Little Fenna' exhibits a compact and very well-branched plant habit with dense foliage.

3. 'Little Fenna' exhibits sturdy branches that are not prone to flopping.
4. 'Little Fenna' exhibits new growth that is pink in color.

The parent plant of 'Little Fenna' is similar to 'Little Fenna' in having a compact plant habit, a short plant height and mature leaves that are green in color. The parent plant of 'Little Fenna' differs from 'Little Fenna' in having young foliage shoots that are bronze-red in color, less branching, and weaker branches that are more floppy. 'Little Fenna' can also be most closely compared to the *Photinia* cultivars 'Red Robin' (not patented) and 'Oploo5' (U.S. Plant Pat. No. 26,578). 'Red Robin' differs from 'Little Fenna' in having a less compact plant habit and young foliage shoots that are brown-red in color. 'Oploo5' differs from 'Little Fenna' in having a taller plant height and variegated leaves.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listing by Plantipp and Visions.

BRIEF DESCRIPTION OF THE DRAWINGS

The accompanying color photographs illustrate the overall appearance and distinct characteristics of 2-year-old plants of the new *Photinia* as grown in an unheated greenhouse in 13-cm containers in Boskoop, The Netherlands.

The photograph in FIG. 1 provides a view of the overall habit of 'Little Fenna'.

Figure 1:
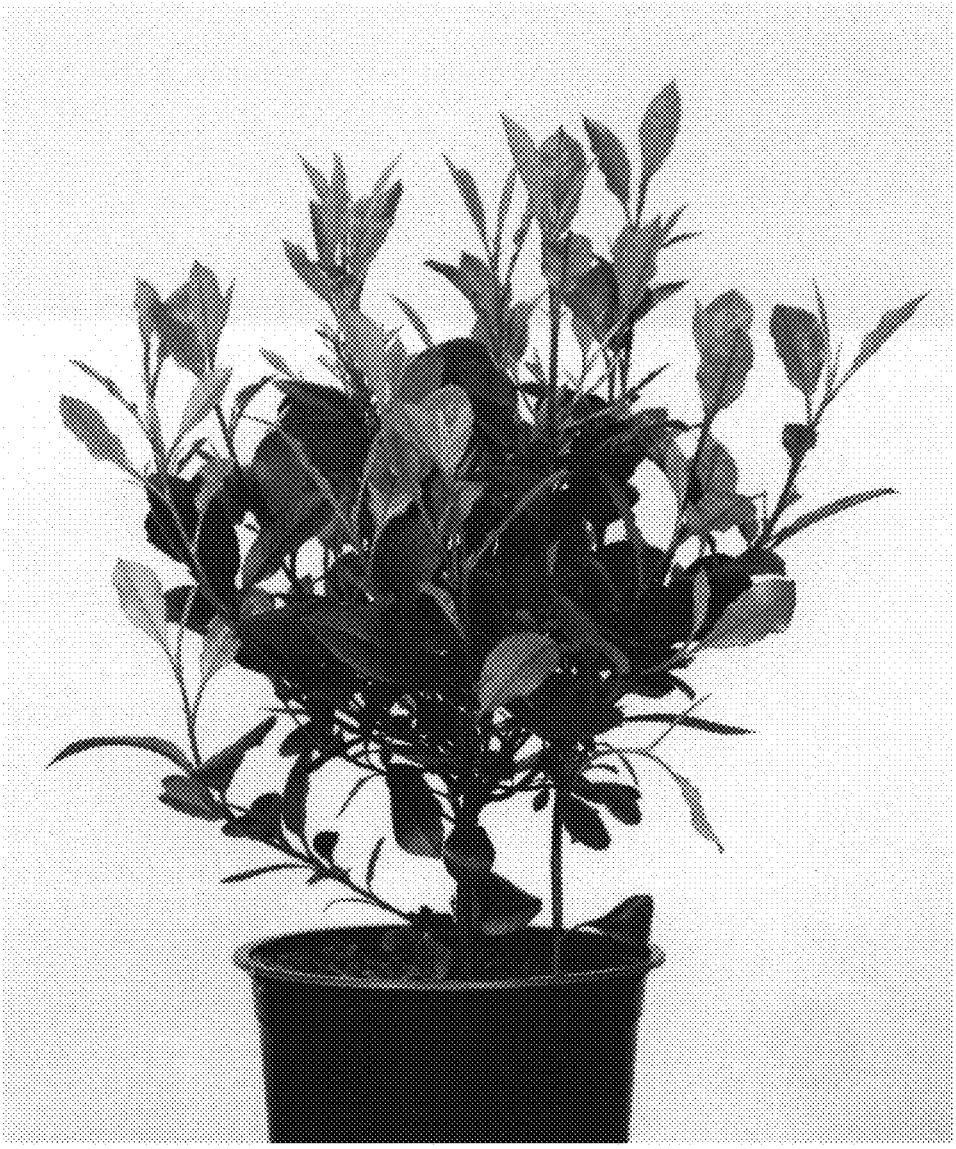
Figure 2:
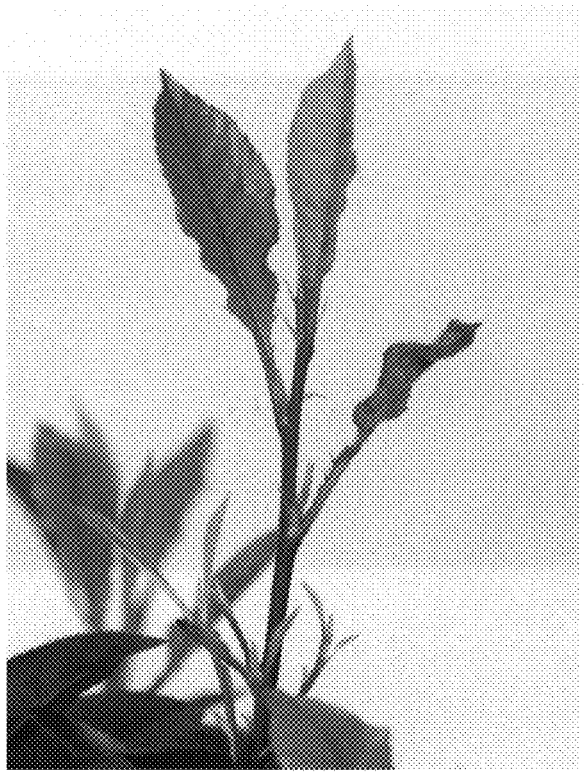

The photograph in FIG. 2 provides a close-up view of young foliage of 'Little Fenna'.

Figure 3:
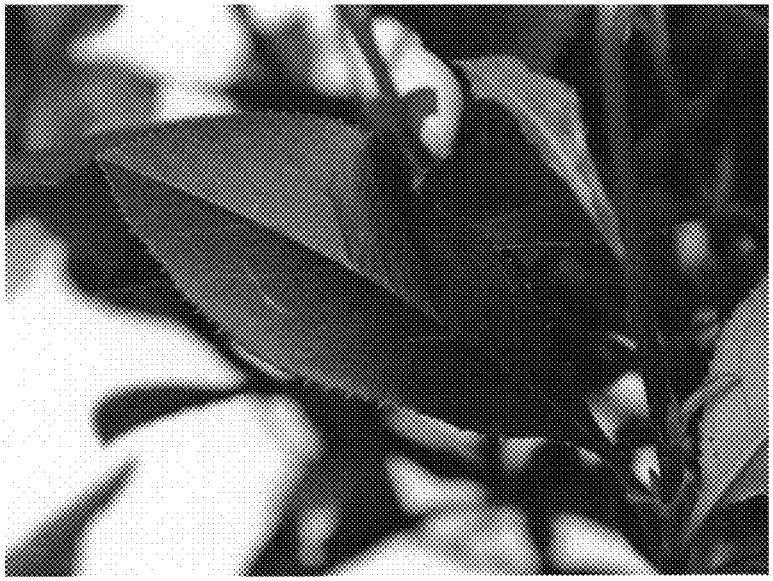

The photograph in FIG. 3 provides a close-up view of the mature foliage of 'Little Fenna'.

The colors in the photographs are as close as possible with the digital photography techniques available and the color values cited in the detailed botanical description most accurately describe the colors of the new *Photinia.*

DETAILED BOTANICAL DESCRIPTION

The following is a detailed description of two-year-old plants of the new *Photinia* as grown outdoors in 13-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Evergreen, perennial bushy shrub.

*Plant habit*.—Broadly upright and compact.

*Plant shape*.—Broadly obovate to nearly spherical.

*Height and spread*.—Average of 32.9 cm in height, 30.8 cm in spread as a 2-year-old plant in a container, a mature plant in the landscape reaches 80 cm in height and 70 cm in spread.

*Cold hardiness*.—At least to U.S.D.A. Zone 7.

*Diseases and pests*.—No susceptibility or resistance to diseases or pests has been observed.

*Rooting habit*.—Fibrous, fine and dense.

*Propagation*.—Semi-hardwood stem cuttings.

*Root development*.—8 weeks to initiate roots, 16 weeks to produce a young plant from a rooted cutting.

*Growth rate*.—Moderate to low.

Stem description:

*Shape*.—Rounded.

*Stem color*.—Young; between N45A and 53A, mature; between 165A and 166B, sunny side tinged with 187B.

*Stem size*.—An average of 13.9 cm in length and 2 mm in width.

*Stem surface*.—Moderately glossy, glabrous.

*Branching*.—Main stems grow from the base, an average of 2 main branches, 30 lateral branches per main branch, strong in strength.

*Branch angle*.—An average of 40° to vertical.

*Branch internode length*.—Average of 1.3 cm.

Foliage description:

*Leaf shape*.—Obovate to broadly obovate.

*Leaf division*.—Simple.

*Leaf base*.—Attenuate.

*Leaf apex*.—Short apiculate.

*Leaf venation*.—Pinnate, upper surface color; 143A, lower surface color; 144B, secondary veins 146A.

*Leaf margins*.—Serrate, slightly and coarsely undulate.

*Leaf arrangement*.—Alternate.

*Leaf attachment*.—Petiolate.

*Leaf quantity*.—Average of 11 per lateral branch.

*Leaf surface*.—Upper and lower surface; smooth, glabrous, leathery, upper surface slightly glossy, lower surface dull.

*Leaf size*.—Average of 6.2 cm in length and 3.3 cm in width.

*Leaf color*.—Young leaves upper surface; between 50A and 52A, young leaves lower surface; 51B, main vein 146D, mature and fall leaves upper surface; between NN137A and 139A, mature and fall leaves lower surface; 146C.

*Petioles*.—Strong, average of 9 mm in length and 2 mm in diameter, both surfaces; 187C in color, smooth, glabrous, moderately glossy.

*Stipules*.—2 leafy stipules present at the base of each petiole, linear in shape, average of 6 mm in length, 1.5 mm in width, entire margins, narrow acuminate apex, cuneate base, both surfaces glabrous and slightly glossy, color; upper surface 147C, changing to 187C at the top, base and margins, lower surface 146C changing to 187C at the top, base and margins.

Flower description: Flowers have not been produced to date.

It is claimed:

1. A new and distinct cultivar of *Photinia* plant named 'Little Fenna', as herein illustrated and described.

* * * * *